United States Patent
Wang

(10) Patent No.: US 10,980,935 B2
(45) Date of Patent: Apr. 20, 2021

(54) ENEMA DEVICE AND METHOD OF USING THE SAME

(71) Applicant: HARVATEK CORPORATION, Hsinchu (TW)

(72) Inventor: Ping-Lung Wang, Hsinchu (TW)

(73) Assignee: HARVATEK CORPORATION, Hsinchu (TW)

( * ) Notice: Subject to any disclaimer, the term of this patent is extended or adjusted under 35 U.S.C. 154(b) by 84 days.

(21) Appl. No.: 15/983,049

(22) Filed: May 17, 2018

(65) Prior Publication Data

US 2019/0151530 A1    May 23, 2019

(30) Foreign Application Priority Data

Nov. 17, 2017   (TW) .................. 106139930

(51) Int. Cl.
| | |
|---|---|
| *A61M 3/02* | (2006.01) |
| *A61M 39/10* | (2006.01) |
| *A61K 31/522* | (2006.01) |
| *A61K 9/00* | (2006.01) |

(52) U.S. Cl.
CPC ......... *A61M 3/0245* (2013.01); *A61K 9/0031* (2013.01); *A61K 31/522* (2013.01);
(Continued)

(58) Field of Classification Search
CPC .............. A61M 3/0245; A61M 3/0266; A61M 2205/584; A61M 2205/36;
(Continued)

(56) References Cited

U.S. PATENT DOCUMENTS

| | | | | |
|---|---|---|---|---|
| 2,786,467 A | * | 3/1957 | Price ..................... | A61M 5/162 604/255 |
| 3,100,487 A | * | 8/1963 | Bathish ............... | A61M 3/0245 604/257 |
| 3,207,298 A | * | 9/1965 | Wilson ................ | A61M 3/0266 206/364 |

(Continued)

FOREIGN PATENT DOCUMENTS

| | | |
|---|---|---|
| CN | 2171360 Y | 7/1994 |
| CN | 2635098 Y | 8/2004 |

(Continued)

OTHER PUBLICATIONS

Teekachunhatean et al, Antioxidant effects after coffee enema or oral coffee consumption in healthy Thai male volunteers, 2012, Human and Experimental Toxicology, 31(7), 643-651 (Year: 2012).*

*Primary Examiner* — Theodore J Stigell
*Assistant Examiner* — Rachel T. Smith
(74) *Attorney, Agent, or Firm* — Li & Cai Intellectual Property (USA) Office

(57) ABSTRACT

An enema device and a method for using the same are disclosed. The enema device includes a non-plastic container and a liquid delivery tube. The non-plastic container is made of glass, stainless steel, or ceramic. The non-plastic container includes a bottom wall and an annular sidewall extending upwardly from the peripheral of the bottom wall, wherein the bottom wall has a bottom planar surface. The liquid delivery tube is in fluid communication with a containing chamber of the non-plastic container. Therefore, harmful effects to the human body from plasticizer can be prevented.

13 Claims, 10 Drawing Sheets

(52) U.S. Cl.
CPC .......... *A61M 3/0266* (2013.01); *A61M 39/10* (2013.01); *A61M 3/022* (2014.02); *A61M 3/0208* (2014.02); *A61M 2202/0468* (2013.01); *A61M 2205/36* (2013.01); *A61M 2205/583* (2013.01); *A61M 2205/584* (2013.01); *A61M 2210/1064* (2013.01); *A61M 2210/1067* (2013.01)

(58) Field of Classification Search
CPC .. A61M 2210/1067; A61M 2210/1064; A61K 9/0031
See application file for complete search history.

(56) References Cited

U.S. PATENT DOCUMENTS 3,329,321 A * 7/1967 Moore ................... B65D 25/32
222/465.1
4,033,347 A * 7/1977 Mapp ................. A61M 3/0241
604/250

FOREIGN PATENT DOCUMENTS

| CN | 2699897 Y | 5/2005 |
|----|-----------|--------|
| CN | 201076632 Y | 6/2008 |
| CN | 205814759 U | 12/2016 |
| CN | 206454054 U | 9/2017 |
| TW | M325422 U | 1/2008 |
| TW | 201043222 A | 12/2010 |
| TW | M557114 U | 3/2018 |

\* cited by examiner

ENEMA DEVICE AND METHOD OF USING THE SAME

BACKGROUND OF THE INVENTION

1. Field of the Invention

The instant disclosure relates to a healthcare product and a method of using the same, and more particularly to an enema device and a method of using the same.

2. Description of Related Art

Similar to the conventional enema, the coffee enema helps to clean the intestines and aids bowel movement. The main difference between the coffee enema and the conventional enema is that the coffee enema process injects a coffee liquid. In general, when coffee travels from the mouth to the large intestines, it would pass through the stomach and the small intestines. However, the tannic acid contained in the coffee can irritate the stomach wall and kill good bacteria in the small intestines. In addition, coffee ingredients can be absorbed by the stomach (upper gastrointestinal tract) and carried directly into the brain and heart by blood circulation, so while people may feel refreshed after drinking coffee, the feeling may also be accompanied by heart palpitations.

In the enema process, the coffee liquid can be injected into the rectum (lower gastrointestinal tract). Accordingly, coffee ingredients such as caffeine and theophylline of the coffee liquid can kill the bad bacteria in the rectum, promote the peristalsis of the large intestines, relax the blood vessels of the large intestinal wall, and treat enteritis. In addition, caffeine and theophylline can be directly absorbed by the rectum and delivered to the liver, so as to increase the activity of glutathione, allow for quick opening of the bile duct, and stimulate the liver to produce detoxification enzymes. Accordingly, detoxification substances of the liver can be smoothly discharged to enhance the detoxification effect. In other words, the coffee enema is based on "hepatic circulation". In the enema process, coffee ingredients can be directly delivered to the liver by the lower gastrointestinal tract and be released after the detoxification reaction, so that heart palpitations can be avoided even if the coffee ingredients should pass through the heart.

However, the conventional enema device uses a plastic container such as a plastic bottle or a plastic enema bag for containing the coffee liquid. Therefore, when a freshly-made coffee liquid is poured into the plastic container, plasticizer could easily be released from the plastic container and cause harmful effects to the human body during the enema procedure. In addition, the conventional enema devices need to be hung at a height and cannot stand on a planar surface, so that it is inconvenient for the coffee liquid to be added into the container.

SUMMARY OF THE INVENTION

In order to solve the aforesaid technical problems associated with the prior art, the instant disclosure provides an enema device and a method of using the same.

One of the embodiments of the instant disclosure provides an enema device which includes a non-plastic container and a liquid delivery tube. The non-plastic container is made of glass, stainless steel, or ceramic. The non-plastic container has a containing chamber for containing a coffee liquid. The non-plastic container includes a bottom and an annular sidewall extending upwardly from the periphery of the bottom wall, and the bottom wall has a bottom planar surface. The liquid delivery tube is in fluid communication with the containing chamber.

Furthermore, the annular sidewall has a tube connector disposed thereon closely adjacent to the bottom wall for connecting to the liquid delivery tube. The tube connector has a position-limiting flange disposed on its periphery.

Furthermore, the outer diameter of the annular sidewall gradually decreases toward the bottom wall, and the annular sidewall has a marking symbol.

Furthermore, the enema device further includes a cover which is detachably coupled to an opening of the non-plastic container.

Furthermore, the enema device further includes a hanging member which is connected to the annular sidewall by a buffering gasket. The non-plastic container is configured to be in a standing state through the bottom planar surface of the bottom wall or in a hanging state through the hanging member.

Furthermore, the enema device further includes a grip portion which is disposed on the annular sidewall.

Furthermore, the enema device further includes a heater for heating the coffee liquid. The annular sidewall has a thermochromic layer coated thereon.

Another one of the embodiments of the instant disclosure provides a method of using the enema device. The method includes the steps of making a coffee liquid by the non-plastic container and introducing the coffee liquid into the large intestine of a user by the liquid delivery tube.

One of the advantages of the instant disclosure is that the enema device and the method of using the same of the instant disclosure can utilize the technical features of "the bottom wall of the non-plastic container has a bottom planar surface" and "the liquid delivery tube is in fluid communication with the containing chamber of the non-plastic container" to prevent plasticizer from entering the intestine via hot coffee liquid, thereby preventing harmful effects to the human body.

To further understand the techniques, means and effects of the instant disclosure, the following detailed descriptions and appended drawings are hereby referred to, such that, and through which, the purposes, features and aspects of the instant disclosure can be thoroughly and concretely appreciated. However, the appended drawings are provided solely for reference and illustration, without any intention to limit the instant disclosure.

BRIEF DESCRIPTION OF THE DRAWINGS

The accompanying drawings are included to provide a further understanding of the instant disclosure, and are incorporated in and constitute a part of this specification. The drawings illustrate exemplary embodiments of the instant disclosure and, together with the description, serve to explain the principles of the instant disclosure.

DETAILED DESCRIPTION OF THE PREFERRED EMBODIMENTS

The instant disclosure provides a novel enema device for healthcare purposes. Embodiments of a silicon carbide crystal and a method for manufacturing the same according to the instant disclosure are described herein. Other advantages and objectives of the instant disclosure can be easily understood by one skilled in the art from the disclosure. The instant disclosure can be applied in different embodiments. Various modifications and variations can be made to various details in the description for different applications without departing from the scope of the instant disclosure. The drawings of the instant disclosure are provided only for simple illustrations, but are not drawn to scale and do not reflect the actual relative dimensions. The following embodiments are provided to describe in detail the concept of the instant disclosure, and are not intended to limit the scope thereof in any way.

Notably, the terms first, second, third, etc., may be used herein to describe various elements or signals, but these elements or signals should not be affected by such elements or terms. Such terminology is used to distinguish one element from another or a signal with another signal. Further, the term "or" as used herein in the case may include any one or combinations of the associated listed items.

First Embodiment

Figure 1:
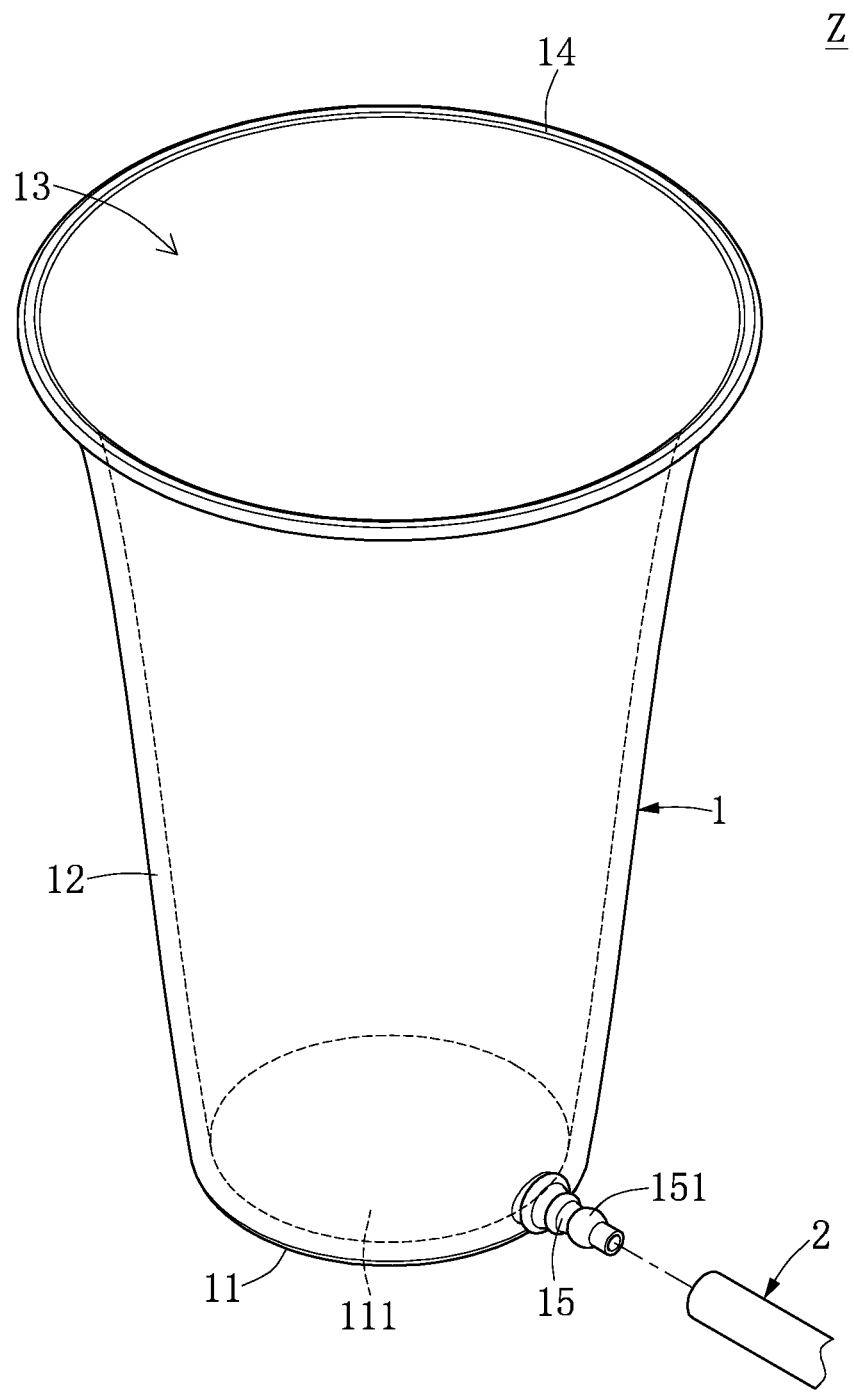
FIG. 1 is a three-dimensional schematic view showing an enema device according to a first embodiment of the instant disclosure.
Figure 2:
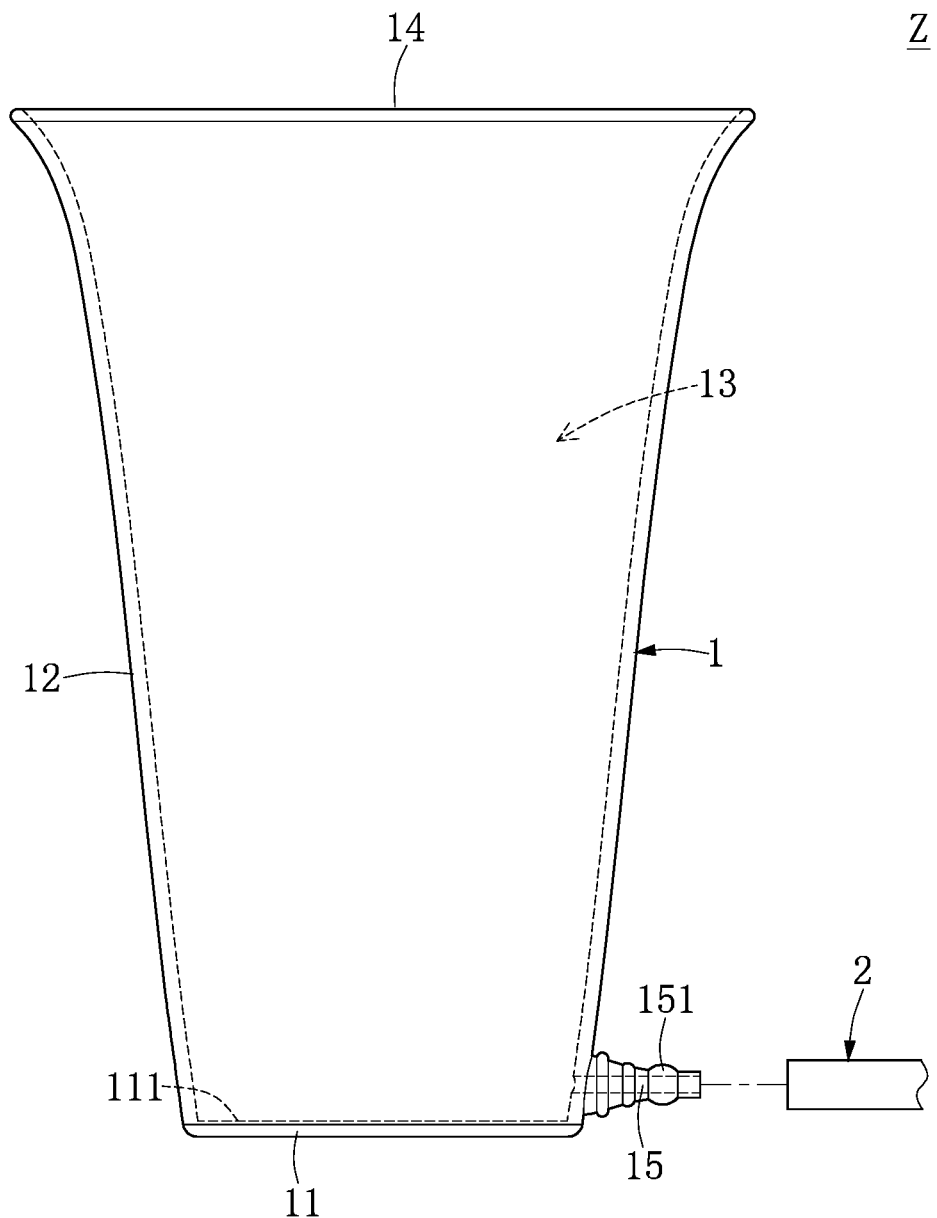
FIG. 2 is a plan schematic view showing the enema device according to the first embodiment of the instant disclosure.
Figure 3:
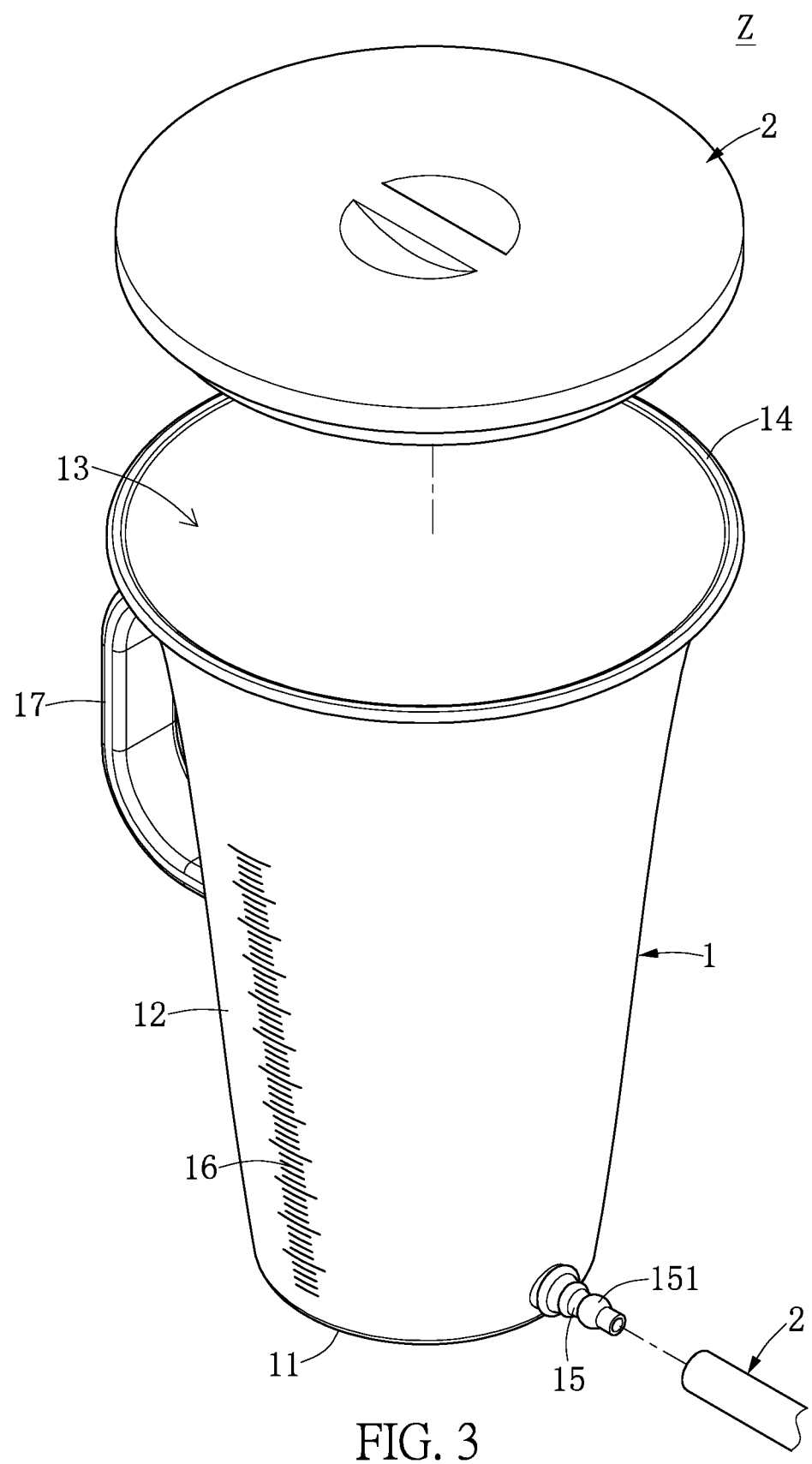
FIG. 3 is a three-dimensional schematic view showing another enema device according to the first embodiment of the instant disclosure.
Figure 4:
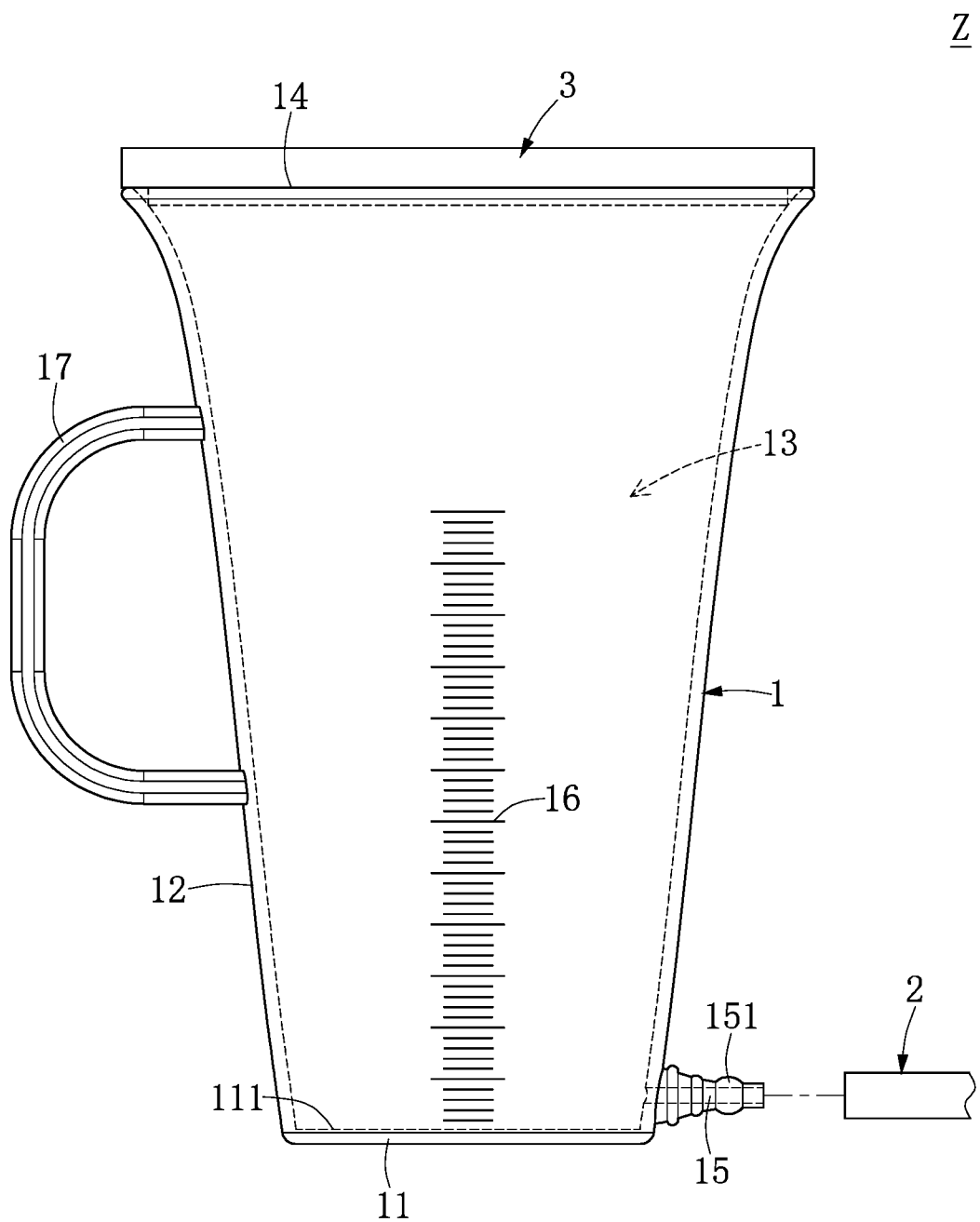
FIG. 4 is a plan schematic view showing another enema device according to the first embodiment of the instant disclosure.
Figure 5:
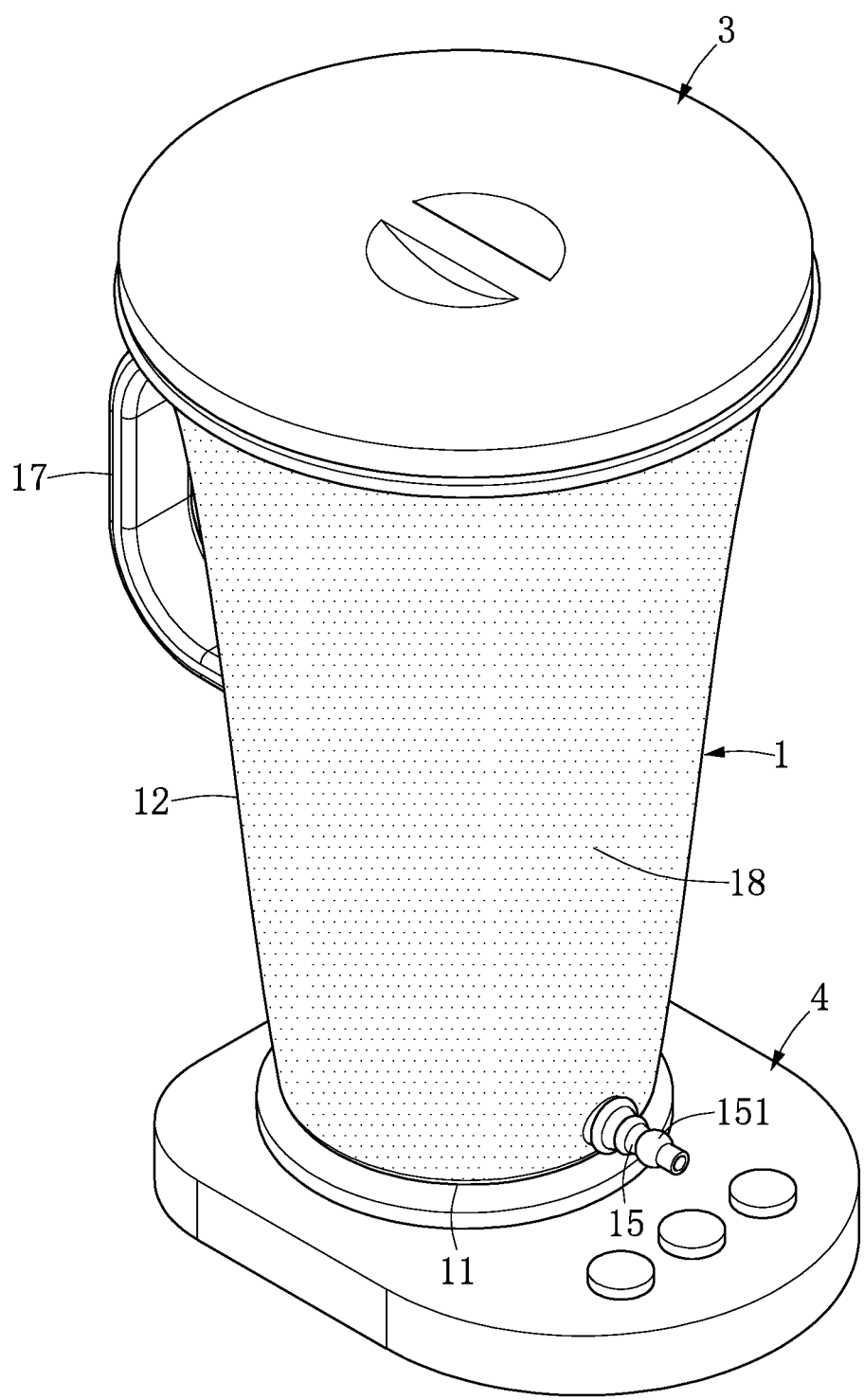
FIG. 5 is a three-dimensional schematic view showing still another enema device according to the first embodiment of the instant disclosure.
Figure 6:
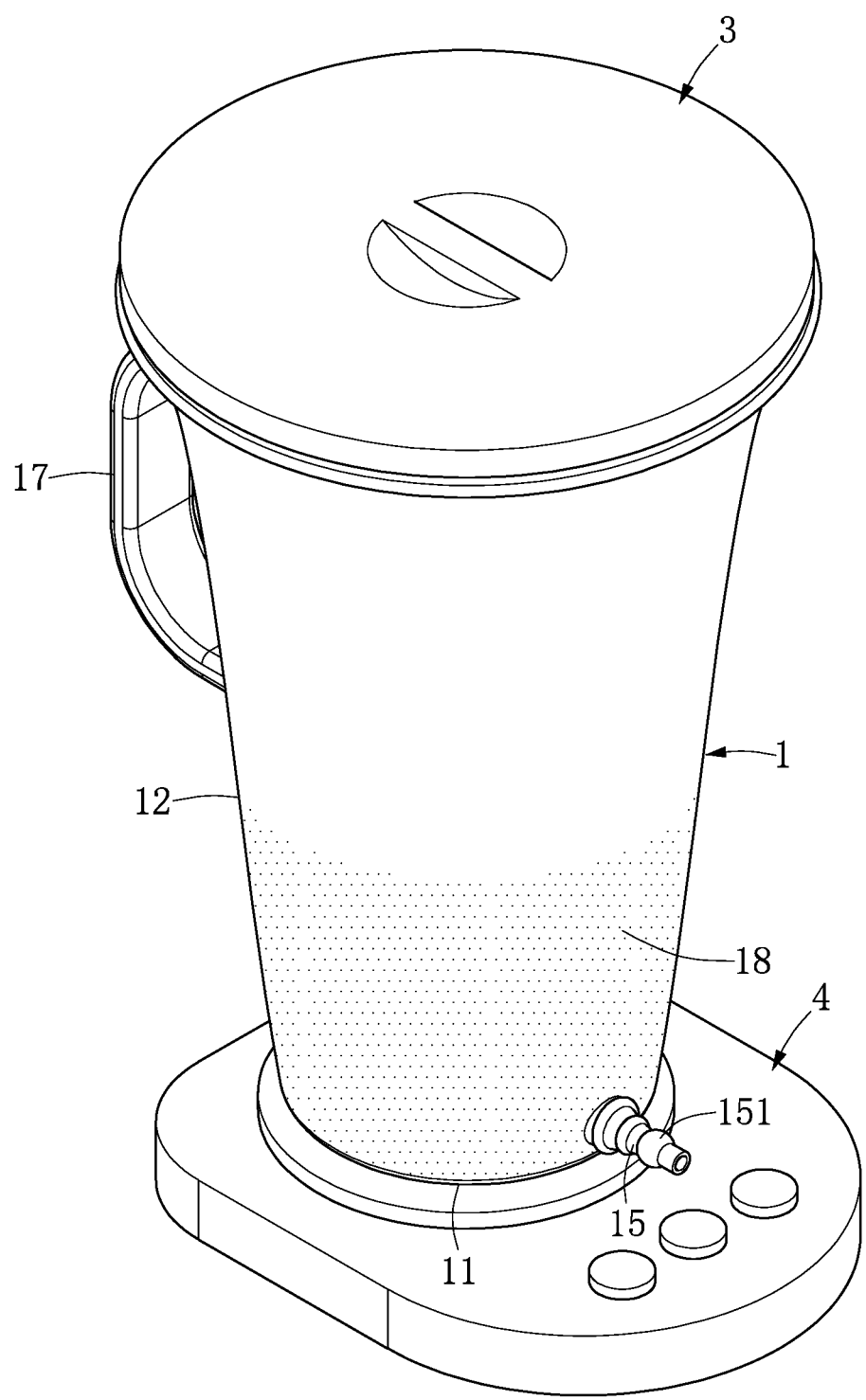
FIG. 6 is a three-dimensional schematic view showing another enema device according to the first embodiment of the instant disclosure.
Figure 7:
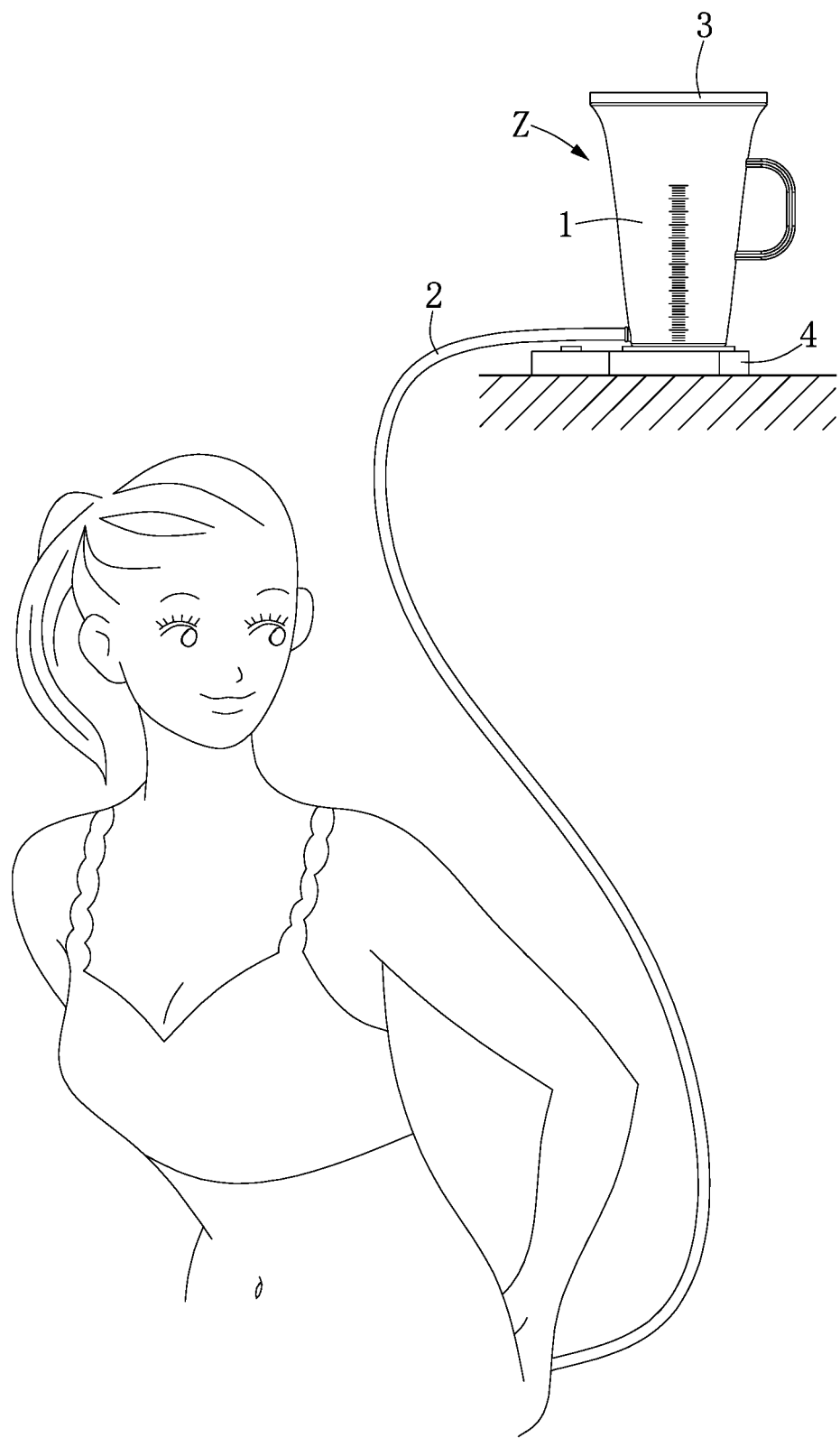
FIG. 7 is a schematic view showing an enema device in use according to the first embodiment of the instant disclosure.

Referring to FIGS. 1 to 7, FIGS. 1, 3, 5 and 6 are three-dimensional schematic views, FIGS. 2 and 4 are plan schematic views, and FIG. 7 is a schematic view showing a usage state. The enema device Z of the instant disclosure includes a glass container 1 and a liquid delivery tube 2. The inventor has discovered that by using a glass container 1 to replace a plastic container such as a plastic bottle or a plastic enema bag for containing a coffee liquid, plasticizer from hot coffee liquid can be prevented from entering the human body and causing harmful effects.

The glass container 1 includes a bottom wall 11 and an annular sidewall 12 extending upwardly from the periphery of the bottom wall 11. The bottom wall 11 and annular sidewall 12 constitute a containing chamber 13 for containing a coffee liquid and an opening 14 arranged above the containing chamber 13. For the sake of convenience, the bottom wall 11 has a bottom planar surface 111 so as to allow the glass container 1 to be in a standing state without any additional support. That is to say, the glass container 1 can stand stably on a supporting platform by the bottom planar surface 111 of the bottom wall 11 thereof. Therefore, the coffee liquid can be easily poured into the glass container 1. Compared with the conventional operation, the user can perform an enema operation by him/herself without having to hang the enema container at a height.

In the present embodiment, the glass container 1 may have a regular or irregular shape. For example, the cross-section of the glass container may be regular or irregular in shape, e.g., circular, elliptical, square, rectangular, polygonal, etc. In order to conveniently add a liquid (e.g., water or coffee) into the containing chamber 13, the outer diameter of the annular sidewall 12 of the glass container 1 gradually decreases toward the bottom wall 11. In addition, in order to accurately control the usage quantity of the coffee liquid, the annular sidewall 12 can have a marking symbol 16. The marking symbol 16, as shown in FIG. 3, can include a plurality of main markings (i.e., larger-scale measurements) and a plurality of auxiliary markings (i.e., smaller-scale measurements) which are alternately arranged with each other, but the instant disclosure is not limited thereto.

Furthermore, the glass container 1 can have a grip portion 17 to increase its convenience and flexibility of use. The grip portion 17, as shown in FIGS. 3 and 4, can be a U-shaped handle and be integrally formed on the annular sidewall 12. The grip portion 17 can have a variety of shapes according to practical requirements. For example, when the coffee liquid would have a relatively high temperature, the shape of the grip portion 17 can be changed so that a safe distance from the annular sidewall 12 can be maintained to prevent the user from being scalded in operation.

The liquid delivery tube 2 is in fluid communication with the containing chamber 13, and is configured to introduce the coffee liquid into the intestine of a human body. More specifically, the annular sidewall 12 of the glass container 1 has a tube connector 15 disposed thereon to connect to the liquid delivery tube 2. The tube connector 15 can be integrally formed on the annular sidewall 12. The periphery of the tube connector 15 can have one or more position-limiting flanges 151 to avoid detachment of the liquid delivery tube 2. Preferably, the tube connector 15 is disposed closely adjacent to an arc edge of the periphery of the bottom wall 11. Accordingly, the coffee liquid within the glass container 1 can be effectively utilized, that is to say, it can be completely discharged from the glass container 1 in an enema operation. In the present embodiment, the liquid delivery tube 2 is a soft silicone tube, but is not limited thereto. The liquid delivery tube 2 can be provided with a flow rate controller (not shown) for controlling a flow rate and a flow velocity of the coffee liquid that is introduced into the intestine.

The enema device Z can further include a cover 3 for preventing dirt or dust from entering the glass container 1, so as to keep the coffee liquid sanitary. In the present embodiment, as shown in FIGS. 3 and 4, the shape of the cover 3 matches with the shape of the opening 14, and the cover 3 is detachably coupled to the opening 14.

It should be noted that the overall enema process may take several hours to complete, so that the coffee liquid needs to be heated and maintained at a constant temperature of between 37° C. and 40° C. to achieve a significant detoxification effect. Therefore, the enema device Z can further include a heater 4 for continuously heating the coffee liquid. In the present embodiment, the heater 4 can be a water bath heater or an electromagnetic heater. When in use, the glass container 1 together with the coffee liquid can be disposed on the heater 4 such that the heater 4 can supply heat to the coffee liquid via the bottom wall 11. Alternatively, the glass container 1 together with the coffee liquid can be disposed in the heater 4 such that the heater 4 can supply heat to the coffee liquid via the bottom wall 11 and the annular sidewall 12.

Preferably, the annular sidewall 12 of the glass container 1 can have a thermochromic layer 18 disposed thereon. The thermochromic layer 18, as shown in FIGS. 5 and 6, can be coated on the entire or a portion of the exterior surface of the annular sidewall 12. When using the heater 4 to heat the coffee liquid, the thermochromic layer 18 can alert the user by a color change. For example, when the coffee liquid has a temperature of below 30° C., the thermochromic layer 18 appears green in color. When the coffee liquid has a temperature of between 30° C. and 35° C., the thermochromic layer 18 appears yellow in color. When the coffee liquid has a temperature of above 35° C., the thermochromic layer 18 appears red in color. Materials of the thermochromic layer 18 are known to a person of ordinary skill in the art and need not be described in detail herein.

Second Embodiment

Figure 8:
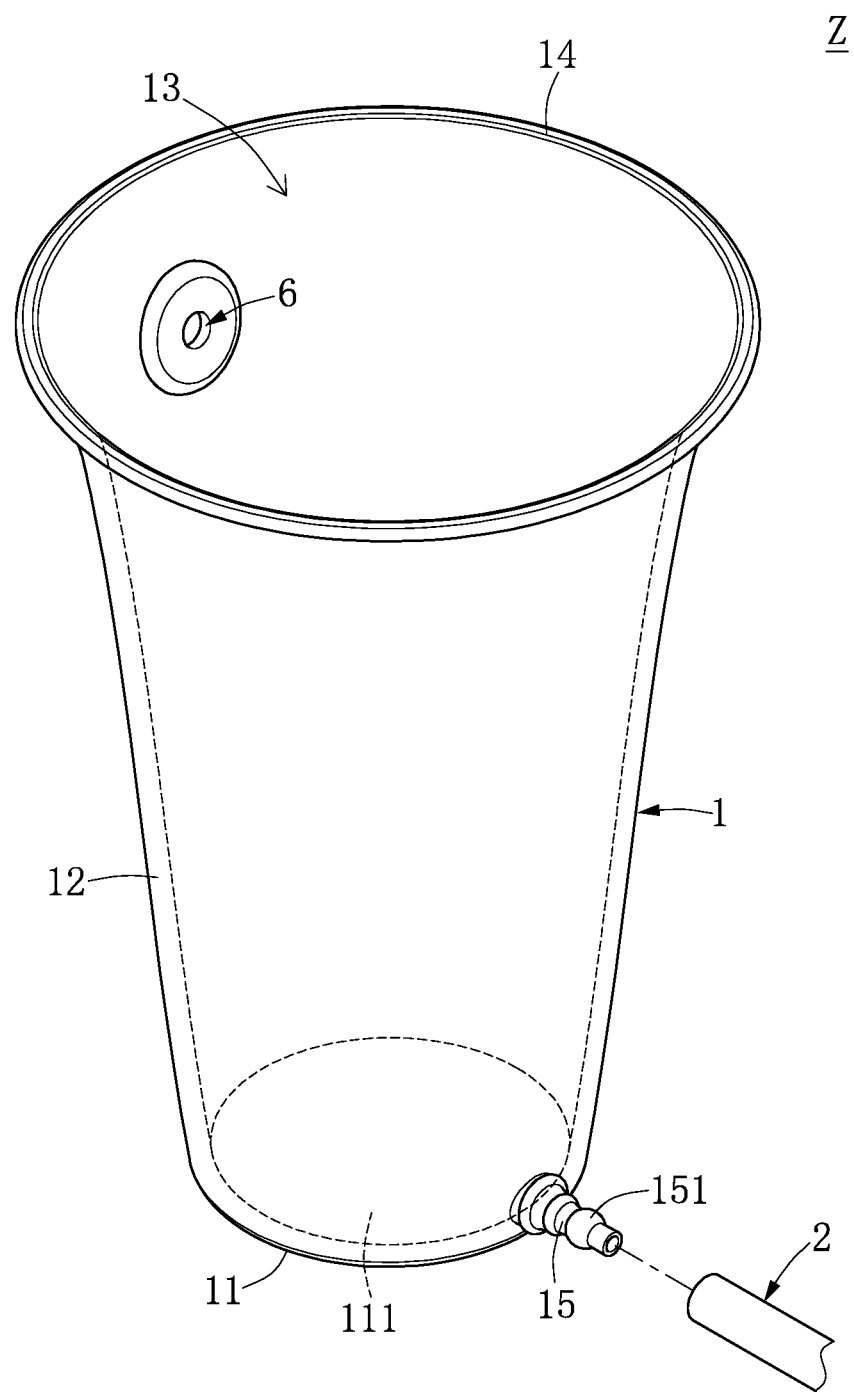
FIG. 8 is a three-dimensional schematic view of an enema device according to a second embodiment of the instant disclosure.
Figure 9:
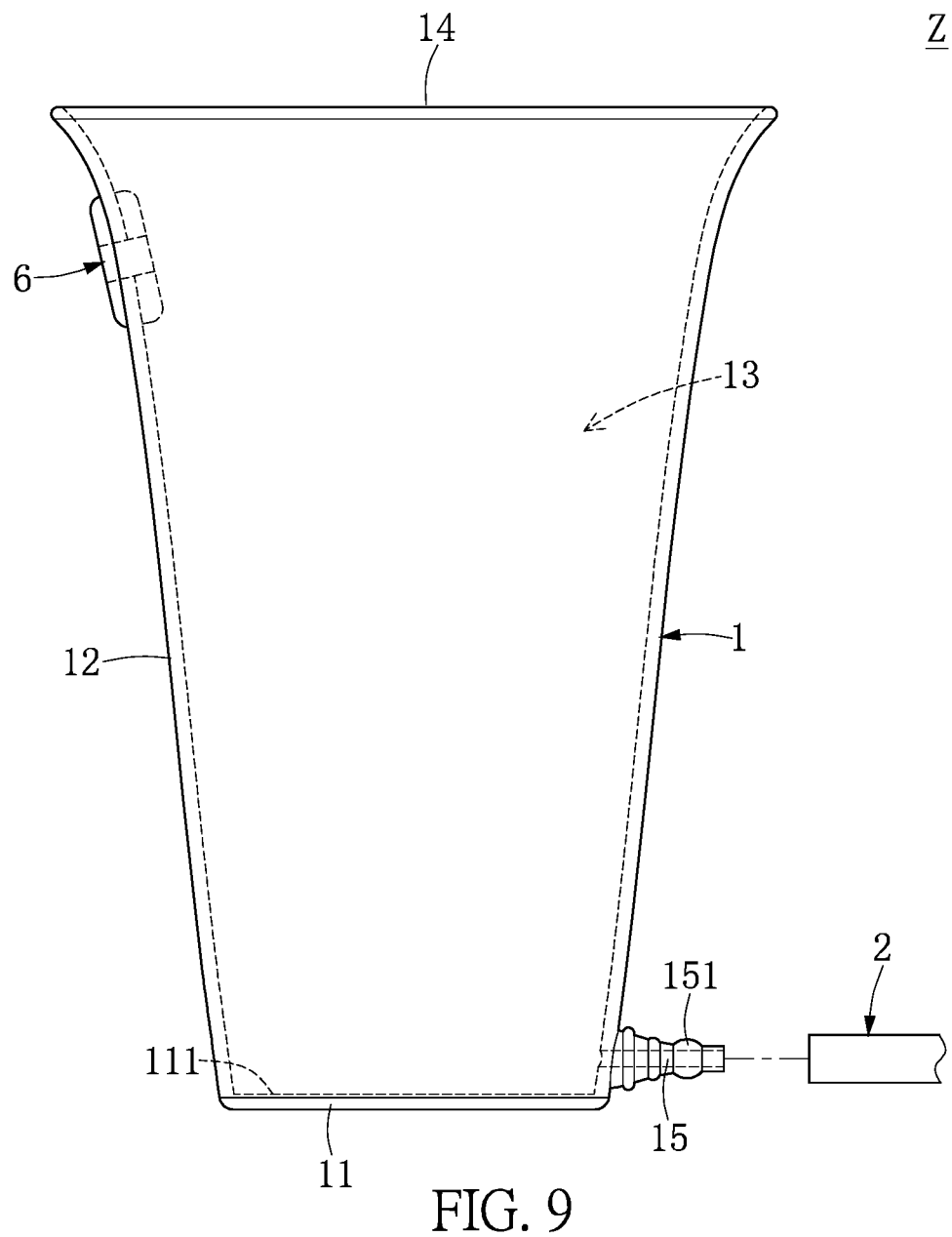
FIG. 9 is a plan schematic view of the enema device according to the second embodiment of the instant disclosure.
Figure 10:
FIG. 10 is a schematic view showing the enema device in use according to the second embodiment of the instant disclosure.

Reference is made to FIGS. 8 to 10, in which FIG. 8 is a three-dimensional schematic view, FIG. 9 is a plan schematic view, and FIG. 10 is a schematic view showing a usage state (inclined hanging state). The main difference between the present embodiment and the first embodiment is that the enema device Z further includes a hanging member 5 and the annular sidewall 12 includes a first sidewall surface and a second sidewall surface opposite to each other. Accordingly, the user can change the usage state of the glass container 1 his/her habits or according to practical requirements. For example, the glass container 1 together with the coffee liquid can be placed in a standing position on a supporting platform or hung at a height, so as to increase convenience in use.

More specifically, the hanging member 5 is connected to the second side of the annular sidewall 12 of the glass container 1 by a buffering gasket 6, and the tube connector 15 is disposed on the first side of the annular sidewall 12 of the glass container 1 and closely adjacent to the bottom wall 11. That is, the hanging member 5 and the tube connector 15 are disposed on two opposite sidewalls of the annular sidewall 12. The hanging member 5 is, for example, an S-type hook, and when in use, one hooking portion abuts against the annular wall 12 by passing through a through-hole of the buffering gasket 6 and another hooking portion hangs onto a fixed position (e.g., a wall surface or a hanger). Further, the buffering gasket 6 and the hanging member 5 are spaced apart from a top edge of the sidewall that is opposite to the tube connector 15 of the annular sidewall 12. Accordingly, the glass container can be in the inclined hanging state by the hanging member 5. It should be understood that the connection manner between the hanging member 5 and the glass container 1 is not limited to the aforesaid manner of the present embodiment. In practice, the hanging member 5 can employ other types of hooks. The buffering gasket 6 can be made of a polymer material such as rubber. Accordingly, the friction between the hanging member 5 and the annular wall 12 can be reduced, so as to ensure a stable and safe operation.

It should be noted that, when performing an enema operation by the enema device Z according to an embodiment of the instant disclosure, the tube connector 15 is disposed closely adjacent to the bottom wall 11, so that the liquid outlet is positioned exactly at the lowest point of the bottom of the glass container 1. Accordingly, the coffee liquid can be completely discharged from the glass container 1. In addition, the step of adding a freshly-made coffee liquid that is poured as the enema liquid into a plastic container can be spared. That is to say, a method of using the enema device Z includes the steps of making a coffee liquid by the glass container 1 and introducing the coffee liquid into the large intestine of a user by the liquid delivery tube 2. Furthermore, in the step of introducing the coffee liquid, the glass container 1 can be set to the standing state, and the coffee liquid can be heated and maintained at a constant temperature of between 37° C. and 40° C.

One of the advantages of the instant disclosure is that the enema device and the method of using the same of the instant disclosure can utilize the technical features of "the bottom wall of the non-plastic container has a bottom planar surface" and "the liquid delivery tube is in fluid communication with the containing chamber of the non-plastic container" to prevent plasticizer from entering the intestine from the hot coffee liquid. Therefore, harmful effects to the human body from the plasticizer can be prevented.

Furthermore, by using the glass container to contain a coffee liquid, the coffee liquid can be heated and maintained at a constant temperature of between 37° C. and 40° C. to achieve a significant detoxification effect. The annular sidewall of the glass container can have a thermochromic layer disposed thereon. When using the heater to heat the coffee liquid, the thermochromic layer can alert the user by a color change.

Incidentally, the example of using the glass container to contain a coffee liquid is only a preferred embodiment of the instant disclosure. Any other container that has resistance to high temperature and that can prevent the harmful effects of plasticizer, e.g., a stainless steel container, a ceramic container, etc., can be used in place of the glass container of the enema device of the instant disclosure.

The aforementioned descriptions merely represent the preferred embodiments of the instant disclosure, without any intention to limit the scope of the instant disclosure which is fully described only within the following claims. Various equivalent changes, alterations or modifications based on the claims of the instant disclosure are all, consequently, viewed as being embraced by the scope of the instant disclosure.

What is claimed is:

1. An enema device, comprising:
a non-plastic container made of glass, stainless steel, or ceramic, and having a containing chamber for containing a coffee liquid, wherein the non-plastic container includes a bottom wall and an annular sidewall extending upwardly from a periphery of the bottom wall, the bottom wall having a bottom planar surface, and the annular sidewall having a first sidewall and a second sidewall opposite to the first sidewall, and wherein a tube connector is disposed on the first sidewall and closely adjacent to the bottom wall;
a liquid delivery tube connected to the tube connector and in fluid communication with the containing chamber; and
a hook connected to the second sidewall of the annular sidewall by passing through a through-hole of a buffering gasket, wherein the buffering gasket is disposed opposite to the tube connector on the second sidewall of the annular sidewall, the buffering gasket and the hook are spaced apart from a top edge of the second sidewall of the annular sidewall so as to allow the non-plastic container to be in an inclined hanging state, and the through-hole passes through the second sidewall;

wherein when the non-plastic container is in the inclined hanging state, a liquid outlet of the tube connector is located at a lowest point of the bottom wall of the non-plastic container.

2. The enema device of claim 1, wherein the tube connector has a position-limiting flange disposed on its periphery.

3. The enema device of claim 1, wherein an outer diameter of the annular sidewall gradually decreases toward the bottom wall, and the annular sidewall has a marking symbol.

4. The enema device of claim 1, further comprising a cover which is detachably coupled to an opening of the non-plastic container.

5. The enema device of claim 1, further comprising a heater for heating the coffee liquid, wherein the annular sidewall has a thermochromic layer coated thereon.

6. A method of using the enema device of claim 1, comprising:
   making the coffee liquid by the non-plastic container; and
   introducing the coffee liquid into intestines of a user by the liquid delivery tube.

7. The method of claim 6, wherein in the step of introducing the coffee liquid, the non-plastic container is in a standing state or an inclined hanging state.

8. The method of claim 6, wherein in the step of introducing the coffee liquid, the coffee liquid is heated and maintained at a constant temperature of between 37° C. and 40° C.

9. An enema device, comprising:
   a glass container having a containing chamber for containing a coffee liquid, wherein the glass container includes a bottom wall and an annular sidewall extending upwardly from a periphery of the bottom wall, the bottom wall having a bottom planar surface, and the annular sidewall having a first sidewall and a second sidewall opposite to the first sidewall, and wherein a tube connector is disposed on the first sidewall and closely adjacent to the bottom wall;
   a liquid delivery tube connected to the tube connector and in fluid communication with the containing chamber; and
   a hook connected to the second sidewall of the annular sidewall by passing through a through-hole of a buffering gasket, wherein the buffering gasket is disposed opposite to the tube connector on the second sidewall of the annular sidewall, the buffering gasket and the hook are spaced apart from a top edge of the second sidewall of the annular sidewall so as to allow the glass container to be in an inclined hanging state and the through-hole passes through the second sidewall;
   wherein when the glass container is in the inclined hanging state, a liquid outlet of the tube connector is located at a lowest point of the bottom wall of the glass container.

10. The enema device of claim 9, wherein the tube connector has a position-limiting flange disposed on its periphery.

11. The enema device of claim 9, wherein an outer diameter of the annular sidewall gradually decreases toward the bottom wall, and the annular sidewall has a marking symbol.

12. The enema device of claim 9, further comprising a cover which is detachably coupled to an opening of the glass container.

13. The enema device of claim 9, further comprising a heater for heating the coffee liquid, wherein the annular sidewall has a thermochromic layer coated thereon.

\* \* \* \* \*